(12) United States Patent
Jones et al.

(10) Patent No.: US 9,090,494 B2
(45) Date of Patent: Jul. 28, 2015

(54) STABILIZED BIOCIDAL COMPOSITION

(75) Inventors: Chris Jones, Cheslyn Hay (GB); Stephanie Edmunds, Willenhall (GB); Alan Fellows, Yardley (GB)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 13/257,174

(22) PCT Filed: Feb. 1, 2010

(86) PCT No.: PCT/EP2010/051194
§ 371 (c)(1), (2), (4) Date: Oct. 25, 2011

(87) PCT Pub. No.: WO2010/105872
PCT Pub. Date: Sep. 23, 2010

(65) Prior Publication Data
US 2012/0046248 A1    Feb. 23, 2012

Related U.S. Application Data

(60) Provisional application No. 61/160,540, filed on Mar. 16, 2009.

(51) Int. Cl.

| | |
|---|---|
| A01P 1/00 | (2006.01) |
| A01N 25/22 | (2006.01) |
| A01N 33/12 | (2006.01) |
| A01N 37/44 | (2006.01) |
| A01N 37/46 | (2006.01) |
| A01N 57/34 | (2006.01) |
| C02F 1/50 | (2006.01) |
| A01N 57/20 | (2006.01) |
| C02F 5/10 | (2006.01) |
| C02F 103/36 | (2006.01) |

(52) U.S. Cl.
CPC . *C02F 1/50* (2013.01); *A01N 57/20* (2013.01); *A01N 57/34* (2013.01); *C02F 5/10* (2013.01); *C02F 2103/365* (2013.01); *C02F 2303/04* (2013.01)

(58) Field of Classification Search
None
See application file for complete search history.

(56) References Cited

FOREIGN PATENT DOCUMENTS

| | | | |
|---|---|---|---|
| WO | WO9933345 | | 4/1999 |
| WO | WO 9933345 A1 | * | 7/1999 |
| WO | WO 9962819 A1 | * | 12/1999 |

OTHER PUBLICATIONS

Ya, L. et al., "Reaction mechanism of tetrakis hydroxymethyl phosphonium with collagen protein." J. Soc. Leather Technologists Chemists 90:214-216 (2006)—copy provided in OA mailed Sep. 5, 2012.*

Ya, L. et al., "Reaction mechanism of tetrakis hydroxymethyl phosphonium with collagen protein." J. Soc. Leather Technologists Chemists 90:214-216 (2006).*

Bolboaca et al., "Amino acids sequence analysis on collagen," Bull. USAMV-CN 63-64: 311-316 (2007).*

* cited by examiner

*Primary Examiner* — Julie Ha
*Assistant Examiner* — Kristina M Hellman
(74) *Attorney, Agent, or Firm* — Hunton & Williams LLP

(57) ABSTRACT

The current invention relates to a process for stabilising a phosphorus-containing compound aqueous composition, comprising the step of adding to the composition an efficient arsenic stabilizing amount of a compound selected from the group consisting of ammonia, ammonium salt, organic amino acid, peptide and polypeptide; application of the stabilized composition for treating an aqueous system optionally containing or in contact with metal sulphide scale, which method comprises adding to the system, separately or together, an efficient anti-scale amount of a stabilized aqueous composition or for treating a water system to kill or inhibit the growth of micro organisms comprising applying thereto or forming in situ an efficient inhibiting amount of the stabilized aqueous composition.

13 Claims, No Drawings

STABILIZED BIOCIDAL COMPOSITION

CROSS-REFERENCE TO RELATED APPLICATIONS

This application is the U.S. National Phase of International Application No. PCT/EP2010/051,194 filed on Feb. 1, 2010, which claims priority to U.S. Provisional Application No. 61/160,540 filed Mar. 16, 2009.

FIELD OF THE INVENTION

The current invention relates to a stabilized biocidal composition. More particularly, the current invention relates to a stabilized biocidal composition containing a phosphorus-containing compound (especially a phosphonium salt), a process for the preparation of such a phosphorus-containing compound, especially a phosphonium salt of tris(hydroxymethyl) phosphine and its use for treating a water system to kill or inhibit the growth of micro organisms and preventing or alleviating the problems which are commonly associated with deposits of metal sulphides, such as iron sulphide.

BACKGROUND

Thus, It is known that tris(hydroxymethyl) phosphine and salts thereof (referred collectively herein as THP) are capable of solubilizing iron sulphide by forming a coloured water-soluble complex. THP based products, especially the sulphate salt (THPS), are commonly added to oil wells as biocides. THP based products are highly effective at controlling sulphate-reducing bacteria, whose activity may be responsible for the original formation of the iron sulphide deposits.

Phosphate rock is the main source of phosphorus for use in the manufacture of organic phosphorus compounds, and typically phosphate rock contains impurities such as arsenic. The arsenic content in phosphate rock varies geographically. At very low levels, typically less than 10 ppm in the phosphate ore, the presence of arsenic does not cause any processing problems or "end-use/application" problems with downstream formulated products. Depending upon the downstream processing, variable amounts of arsenic will be still be present in finished phosphorus compounds/products. However, higher levels of arsenic, in the original phosphate rock can be carried through downstream processing and, can result in product instability and discoloration and/or precipitation.

Chinese sourced phosphate rock which is becoming one of main sources of phosphorus ores, typically contains 20-60 ppm arsenic and, in many instances, this is sufficient to result in an unacceptable discoloration of aqueous solutions of phosphorus-containing and/or precipitation of a problematic red/brown solid comprising elemental arsenic or arsenic compounds which is both unsightly and commercially unacceptable. Such precipitates would block filters, accumulate in tanks and form sludge. A concentration by weight above 1 ppm, typically above 5 ppm and certainly above 15 ppm of arsenic in the phosphorus-containing compound aqueous composition can generate the above mentioned problems, knowing that such weight concentration can reach 50 ppm and even more.

Thus, there exists a constant need in having aqueous stabilized phosphorus-containing compounds, more particularly, compositions wherein the arsenic impurity has been eliminated or at least alleviated totally or in part.

SUMMARY OF THE INVENTION

The invention satisfies at least one of the needs expressed above.

In fact, after extensive research and development work, the Applicant has surprisingly found out and developed a solution which can prevent or, at the very least, minimise, the precipitation of arsenic or arsenic based compounds from aqueous stabilized phosphonium compositions.

The current invention relates to a process for stabilizing a phosphorus-containing compound, more particularly a phosphonium salt, aqueous composition, comprising the step of adding to said composition an efficient arsenic stabilizing amount of a compound selected from the group consisting of ammonia, ammonium salt, organic amino acid, peptide (compounds with —CO—NH— unit) and polypeptide.

The current invention also relates to a stabilized aqueous composition comprising a phosphorus-containing compound, more particularly a phosphonium salt containing arsenic, and an efficient arsenic stabilizing amount of a compound selected from the group consisting of ammonia, ammonium salt, organic alpha-amino acid, peptide and polypeptide.

According to another aspect, the current invention relates to a method for treating a water system to kill or inhibit the growth of micro organisms comprising applying thereto or forming in situ an efficient inhibiting amount of the stabilized aqueous composition of the current invention. The water system can be for example an oil field produced water, injection water, drilling fluids or water for hydrostatic testing of pipelines, a paper mill thin stock or backwater, an industrial processing or cooling water, a geothermal or desalinated water or feed stream or a surface which is disinfected.

According to one more aspect, the current invention relates to a method of treating an aqueous system containing or in contact with metal sulphide scale, which method comprises adding to said system, separately or together, an efficient anti-scale amount of a stabilized aqueous composition of the current invention, contacting said scale with said aqueous composition, thereby dissolving at least part of said scale in said aqueous composition and withdrawing said dissolved scale from the system.

DETAILED DESCRIPTION OF PREFERRED EMBODIMENTS

Preferably, the phosphorus-containing compound is a phosphonium compound having arsenic as impurity, especially a tetrakis(hydroxyorgano)phosphonium salt or compound of formula (I)

$$[R'R''(CH_2OH)_2P^+]_n X^- \qquad (I)$$

wherein:
n is the valency of X;
R' and R", which may be the same or different, are selected from an alkyl, hydroxyalkyl, alkenyl or aryl moiety and X is an anion.
R' and R" have preferably between 1 and 20 carbon atoms.
X is preferably selected from the group consisting of chloride, sulphate, phosphate, acetate, oxalate and bromide.

Most preferably, the phosphonium compound is tetrakis (hydroxymethyl) phosphonium sulphate mentioned herein below as THPS. Generally speaking, tetrakis(hydroxymethyl) phosphonium salts are mentioned herein below as THP+.

Alternatively, the phosphonium compound may be, for example, a tetrakis(hydroxymethyl) phosphonium chloride, tetrakis(hydroxymethyl) phosphonium bromide, tetrakis(hydroxymethyl)phosphonium phosphate, tetrakis(hydroxymethyl)phosphonium acetate or tetrakis(hydroxymethyl)phosphonium oxalate.

Alternatively, the phosphorus-containing compound may be an alkyl-substituted phosphine, e.g. tris(hydroxymethyl) phosphine as shown in formula (II):

(CH$_2$OH R$_2$)P           (II)

wherein:
each R, which may be the same or different, is selected from a alkyl, hydroxyalkyl, alkenyl or aryl moiety having preferably between 1 and 20 carbon atoms.

Typically, the arsenic content in the phosphorus-containing compound is above 5 ppm which can lead to a weight concentration above 1 ppm, typically above 5 ppm and certainly above 15 ppm of arsenic in the phosphorus-containing compound aqueous composition and can reach 50 ppm and even more as mentioned above. On average, the aqueous composition comprising a phosphorus-containing compound has a weight concentration of arsenic between 1 and 100 ppm, more particularly, between 5 and 50 ppm and even more.

Typically, the weight concentration of the phosphonium compound in the aqueous composition to be stabilized is between 5 and 75, preferably between 15 and 70.

The efficient arsenic stabilizing amount of the compound selected from the group consisting of ammonia, ammonium salt, organic amino acid, peptide (compounds with —CO—NH— unit) and polypeptide, usually represents a concentration of between 40 and 10,000 ppm, preferably 75 and 5000 ppm, and most preferably 100- 1000 ppm of arsenic stabilizing compound in said aqueous composition.

It is recommended to set the pH of the aqueous composition to be stabilized to a value below 7 and, preferably, between 6 and 3 with a diluted mineral acid (e.g. sulphuric acid, phosphoric acid, nitric acid or hydrogen halide) or an organic acid (e.g. formic acid or acetic acid). Then, the arsenic stabilizing compound is being added to said composition.

As ammonium salt, it is recommended to use ammonium chloride or bromide.

As organic amino acid, it is recommended to use alanine, beta-alanine, cystathionine, cystine, histidine, glycine, leucine, isoleucine, histidine, lysine, methionine, proline, sarcosine, serine tyronine, tyrosine and valine.

The instant invention also relates to a stabilized aqueous composition by the method of the current invention, comprising a phosphorus-containing compound, more particularly a phosphonium salt containing arsenic, and an efficient arsenic stabilizing amount of a compound selected from the group consisting of ammonia, ammonium salt, organic alpha-amino acid, peptide and polypeptide.

The stabilized aqueous compositions of the instant invention are useful for treating aerobic or anaerobic water systems contaminated or liable to be contaminated with microorganisms. For example they are effective against problematic organisms such as general heterotrophic bacteria in oilfield water systems, cooling water systems, industrial process water, paper processing systems, geothermal water, central heating and air conditioning systems, for controlling algae in industrial water systems, lakes, streams, canals and reservoirs, and for treating cooling water in power stations and for marine engines. The stabilized aqueous compositions are particularly useful in killing sulphate reducing bacteria in the above systems, and especially in oil field produced water, injection water, drilling fluids or water for hydrostatic testing. They are also useful as preservatives in aqueous based formulations such as bitumen and tar emulsions, paper sizes, adhesives, paints, cellulosic pulps including pulp thin stock and backwash recirculating liquor. The stabilized aqueous compositions are useful in disinfectants including farmyard, domestic and surgical disinfectants. They may be used in the fumigation of grain silos, crops and crop storage areas. The stabilized aqueous compositions are useful for protecting plants against fungi, bacteria, viruses and other microbial plant pathogens, by application to the plants and or to the soil in which they are growing or to be grown, or for use in a seed dressing.

The stabilized aqueous composition are supplied as concentrates at a weight concentration of about 5 to 75% by weight concentration and can be optionally blended with other functional additives such as antifoams, surfactants and co-biocidal compounds, such as aldehydes. The stabilized aqueous compositions maybe either continuously dosed into a water system or batch dosed as required. Alternatively, it may be diluted to a concentration of from 0.001 to 10%, preferably 0.01 to 0.1% by wt. before application.

According to another aspect, the current invention relates to a method of treating an aqueous system containing or in contact with metal sulphide scale, which method comprises adding to said system, separately or together, an efficient anti-scale amount of a stabilized aqueous composition of the current invention, contacting said scale with said aqueous composition, thereby dissolving at least part of said scale in said aqueous composition and withdrawing said dissolved scale from the system.

In that specific application, the stabilized aqueous composition of the phosphonium compound maybe used as a continuous treatment into a water system or batch dosed as required. Alternatively, it may be diluted to a concentration of from 0.001 to 10%, preferably 0.01 to 0.1% by wt. before application.

Iron sulphide deposits are a major source of economic loss in the oil industry. These deposits are mainly the result of reaction between hydrogen sulphide, often produced as a metabolic byproduct, by sulphate reducing bacteria, and ferrous metal oilfield equipment and/or iron compounds in the formation. They obstruct the flow of oil through wells, in the adjacent strata and also in pipelines and in processing and refinery plant. Iron sulphide particles also tend to stabilise oil-water emulsions which often form, especially during secondary oil recovery, and present major problems to oil producers. In that specific application the stabilized aqueous composition of the current invention may also include other water treatment products such as anionic, cationic, amphoteric and non-ionic surfactants and wetting agents. The formulation may additionally contain biocides, (for example, formaldehyde or glutaraldehyde) dispersants, demulsifiers, antifoams, solvents, scale inhibitors, corrosion inhibitors, gas hydrate inhibitors, asphaltene inhibitors, naphthenate inhibitors, oxygen scavengers and/or flocculants. The compositions may also comprise non-surfactant biopenetrants including any of those described in WO99/33345.

The invention is further illustrated by the following examples.

EXAMPLES 1-4 AND COMPARATIVE EXAMPLE 5:

In all the examples the same phosphorus-containing compound aqueous composition whose phosphonium compound is tetrakis(hydroxymethyl) phosphonium sulphate (THPS) is stabilized by different arsenic stabilizing compounds.

That aqueous composition is at a 50% by wt. THPS concentration and a 30 ppm by weight arsenic concentration.

Four samples (examples 1-4) are stabilized with stabilizing compounds at different concentrations and the last one is not stabilized at all.

The efficiency of the arsenic stabilizing compounds is determined by the measurement of the time at which an arsenic compound precipitate can be seen.

That precipitate is assessed by visual observations with time at ambient temperatures (25° C.).

Without treatment, the 50% THPS formulation develops a red precipitate within 5 days.

The results are summarised in table 1 herein below:

TABLE 1

| example | Arsenic Stabilizing Compound | Concentration of Arsenic Stabilizing Compound % | Efficiency |
|---|---|---|---|
| 1 | Glycine | 0.1 | >6 months |
| 2 | Glycine | 0.02 | At least 2 months |
| 3 | Glutathione | 0.2 | At least 5 months |
| 4 | Ammonium Chloride | 0.1 | At least 5 months |
| 5 | None | 0 | Less than 5 days |

Without treatment, the 50% THPS formulation comparative example 5 develops a red precipitate within 5 days.

The invention claimed is:

1. A process for stabilizing an aqueous composition comprising a phosphorus-comprising compound, said process comprising:
adding to said composition an effective amount of an arsenic-stabilizing compound which is the amino acid glycine wherein said phosphorous-comprising compound comprises a phosphonium compound comprising an arsenic impurity and wherein said arsenic-stabilizing compound reduces or prevents precipitation of arsenic from said aqueous composition.

2. The process of claim 1, wherein the phosphonium compound comprises a tetrakis(hydroxyorgano)phosphonium compound of formula:

[R'R"(CH$_2$OH)$_2$P$^+$]$_n$X$^-$ wherein:
n is the valency of X$^-$;
R' and R", which may be the same or different, comprise an alkyl, hydroxyalkyl, alkenyl or aryl moiety, and
X$^-$ is an anion.

3. The process of claim 2, wherein
R' and R" comprise 1 to 20 carbon atoms, and
X$^-$ comprises chloride, sulfate, phosphate, acetate, oxalate or bromide.

4. The process of claim 2, wherein the phosphonium compound comprises a tetrakis(hydroxymethyl) phosphonium salt.

5. The process of claim 2, wherein the phosphonium compound comprises:
tetrakis(hydroxymethyl)phosphonium chloride,
tetrakis(hydroxymethyl)phosphonium bromide,
tetrakis(hydroxymethyl)phosphonium phosphate,
tetrakis(hydroxymethyl)phosphonium acetate,
tetrakis(hydroxymethyl)phosphonium oxalate or
tetrakis(hydroxymethyl) phosphonium sulfate.

6. The process of claim 2, wherein the amount of the phosphonium compound in the aqueous composition to be stabilized ranges from 5 to 75% by weight of the aqueous composition.

7. The process of claim 6, wherein the amount of the phosphonium compound ranges from 20 to 70% by weight of the aqueous composition.

8. The process of claim 1, wherein the amount of arsenic impurity ranges from 1 to 100 ppm.

9. The process of claim 8, wherein the amount of arsenic impurity ranges from 5 to 50 ppm.

10. The process of claim 1, wherein the amount of arsenic-stabilizing compound ranges from 40 to 10,000 ppm in the aqueous composition.

11. The process of claim 10, wherein the amount of arsenic-stabilizing compound ranges from 75 to 5,000 ppm.

12. The process of claim 1, further comprising:
adjusting the pH of the aqueous composition to 7 or less before adding the arsenic stabilizing compound to said composition.

13. The process of claim 12, wherein the adjusted pH ranges from 6 to 3.

* * * * *